CHRYSANTHEMUM PLANT
Filed May 18, 1973
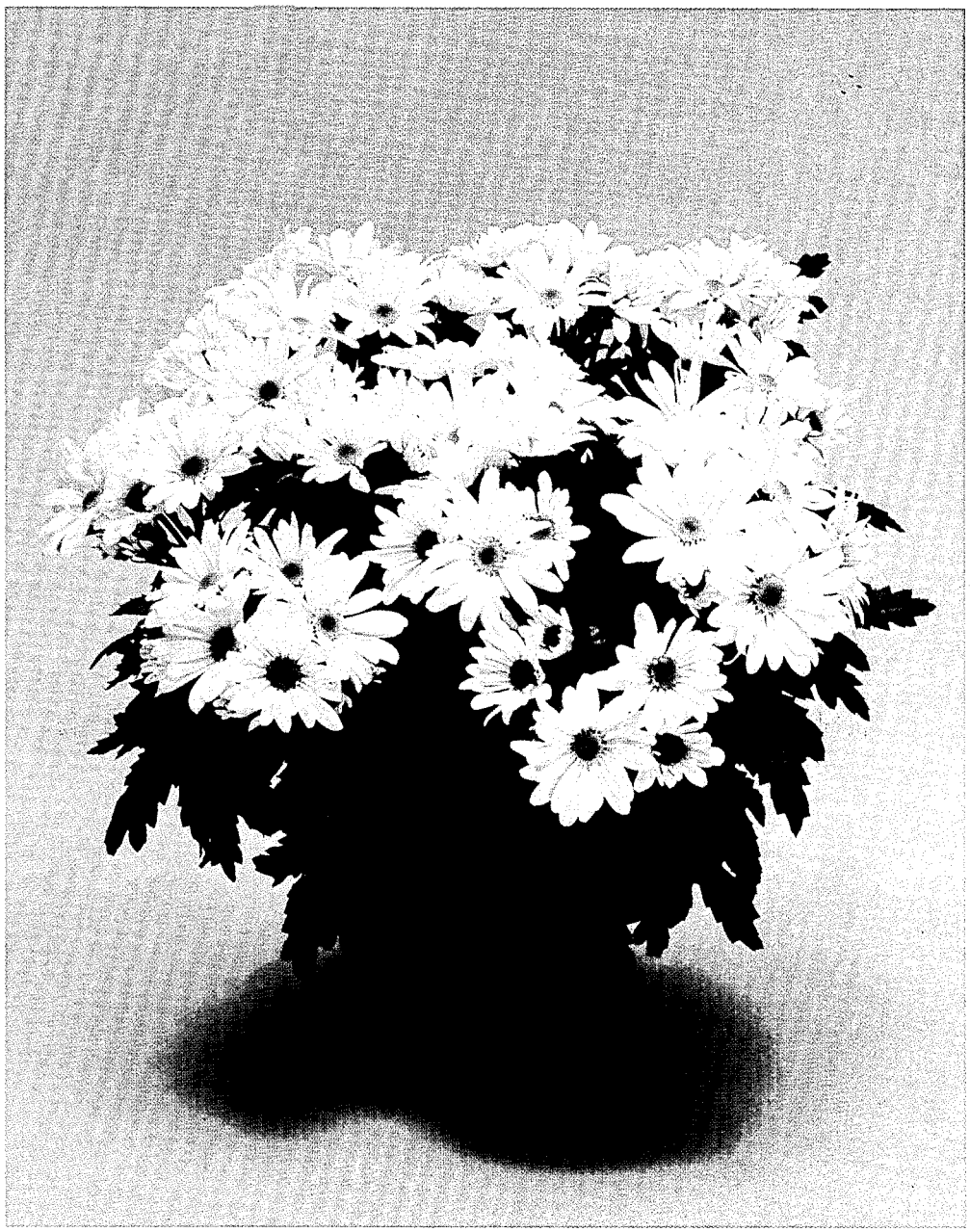

United States Patent Office

Plant Pat. 3,632
Patented Oct. 8, 1974

3,632
CHRYSANTHEMUM PLANT

Walter H. Jessel, Jr., Doylestown, and William E. Duffett, Akron, Ohio, assignors to Yoder Brothers, Inc., Barberton, Ohio

Filed May 18, 1973, Ser. No. 361,440
Int. Cl. A01h *5/00*
U.S. Cl. Plt.—74 1 Claim

The present invention comprises a new and distinct cultivar of chrysanthemum plant known by the varietal name Fiesta which is a seedling of #5732–3×#21580–1. Both parents are unpatented and identified for breeding purposes by the indicated breeding numbers.

The new cultivar is similar in many respects to the well-known unpatented cultivar Yellow Bonnie Jean, and Improved Yellow Bonnie Jean, disclosed in pending U.S. Plant Patent Application Ser. No. 170,936, filed Aug. 11, 1971, in the name of Helmut Gortz, now U.S. Plant Pat. No. 3,404. The new cultivar has the same characteristics of:

1. Use as a tall treatment pot mum.
2. Single, or daisy, flower form.
3. Similar color retention.

The new cultivar is distinguished from Yellow Bonnie Jean and Improved Yellow Bonnie Jean by the following characteristics when grown under comparable conditions:

1. A year round period of value.
2. Approximately 12–16 days earlier response when grown as a pinched spray pot.
3. A semi-spreading habit with approximately 2″ more spread as a pinched plant.
4. Excellent breaking action from a pinch, and will average one more break per plant than Yellow Bonnie Jean and Improved Yellow Bonnie Jean.
5. Approximately 4″ less vigor when grown as a pinched spray pot, in a 4-cutting, 6″ pot given tall treatment and one application of 2500 p.p.m. B–9 approximately 2 weeks after pinching during the various seasons of the recommended use (January through December), as defined in the timetables published by Yoder Brothers, Inc., Barberton, Ohio.

6. A shorter habit thereby making use of the new cultivar as a cut spray not recommended.
7. Less prominent foliar veination.
8. No known sensitivity to commonly used greenhouse chemicals.
9. A unifor flowering response under midwinter conditions.
10. Reduced pollen production.
11. Adaptability to all pot sizes.
12. Fiesta and Yellow Bonnie Jean have a light yellow flower color, whereas Improved Yellow Bonnie Jean has a darker yellow flower color.

The new cultivar was selected from the progeny of the designated cross and when asexually reproduced by cuttings at Barberton, Ohio, has been found to retain its distinctive characteristics through successive propagations.

The new cultivar when grown in the vicinity of Barberton, Ohio, has a response period of approximately 8 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering period in all areas of the United States is year round, except in southern Florida where it is recommended from November through April.

The accompanying photographic drawing of the new cultivar in pot form shows the unique characteristics of the new cultivar, with the color being as nearly true as possible with color illustrations of this type. Color references in the following description are made to the Munsell Color Book, 1963 edition. Comparisons are made with the cultivars Yellow Bonnie Jean and Improved Yellow Bonnie Jean. Where only a single value or description appears for the new cultivar, the same value or description applies to the comparison cultivars as well.

Botanical classification: *Chrysanthemum morifolium*

| | Fiesta | Yellow Bonnie Jean | Improved Yellow Bonnie Jean |
|---|---|---|---|
| Bloom: | | | |
| Size | 2¾″ to 3″ | 3″ to 3¼″ | 3″. |
| Fully expanded | 3¼″ | 3½″ | 3½″. |
| Borne | Clusters on elongated pedicels | | |
| Stems | Short and strong | | |
| Form | Daisy | | |
| Permanence | 10 days | 7 days | 10 days. |
| Color: | | | |
| Center of flower | Green, 2.5GY5/8 to yellow, 7.5Y8/10 | Light green, 2.5GY6/8 to yellow-green, 5Y8.5/10. | Light green, 2.5GY6/8 to light yellow-green, 10Y8.5/10. |
| Base of petals | Yellow-green, 2.5GY6/10 | Yellow-green, 2.5GY6/8 | Yellow, 7.5Y8.5/10 to yellow, 7.5Y8.5/8. |
| Inside of petals | Yellow, 7.5Y8.8/7.2 to pale yellow, 7.8Y9/4. | Light yellow, 7.5Y8.5/8 to pale yellow, 7.5Y9/4. | Do. |
| Reverse of petals | Yellow, 7.5Y8.5/8 to pale yellow, 7.5Y9/4. | Light yellow, 7.5Y9/4 to pale yellow, 7.5Y9/2. | Light yellow, 7.5Y9/6 to light yellow, 7.5Y9/4. |
| Tonality from a distance. | Light yellow | Light yellow | Yellow. |
| Discoloration | Pale yellow, 7.8Y9/4 | Light yellow, 7.5Y9/4 | Yellow, 7.5Y8.5/8. |
| Petals; | | | |
| Texture | Smooth | | |
| Appearance and form | Open at base, broad flat 2-ridged keel, tapering to a blunt tip. | Open at base, broadens quickly, slight longitudinal petal roll, broad shallow keel, tapering to a blunt tip. | Open at base, broadens quickly, slight longitudinal roll, broad shallow keel, tapering to a blunt point. |
| Arrangement | Composite, whorled on a single receptacle. | | |
| Persistence | Resist shatter | | |
| Fragrance | Typical chrysanthemum | | |
| Reproductive organs: | | | |
| Stamen, anthers | 250+ | 250+ | 150 to 200. |
| Pollen | None to abundant (functional sterility). | | |
| Arrangement | Clustered in center of flower, if present. | | |
| Styles | Present both ray and disc florets | | |
| Length | Short | | |
| Ovaries | At the base of petal attached to receptacle. | | |

TABLE—Continued

| | Fiesta | Yellow Bonnie Jean | Improved Yellow Bonnie Jean |
|---|---|---|---|
| Plant: | | | |
| Form | Herbaceous | | |
| Growth | Semi-spreading | Upright | Upright. |
| Height | Approximately 12"-14" when grown as a pinched spray pot, in a 4-cutting, 6" pot given 1 application of 2500 p.p.m. B-9 approx. 2 weeks after pinching and 8 week tall treatment (1-2 weeks of long days) during the various seasons of recommended use (January thru December) as defined in the timetables published by Yoder Brothers, Inc., Barberton, Ohio. | Approximately 16"-18" when grown as a pinched spray pot, in a 4-cutting, 6" pot, given 1 application of 2500 p.p.m. B-9 approx. 2 weeks after pinching and 10 week tall treatment (1-2 weeks of long days) during the various seasons of recommended use (April thru November 15) as defined in the timetables published by Yoder Brothers, Inc., Barberton, Ohio. | Approximately 18"-20" when grown as a pinched spray pot, in a 4-cutting, 6" pot, given 1 application of 2500 p.p.m. B-9 approx. 2 weeks after pinching and 10 week tall treatment (1-2 weeks of long days) during the various seasons of recommended use (April thru November 15) as defined in the timetables published by Yoder Brothers, Inc., Barberton, Ohio. |
| Spread | Approximately 10"-12" when grown as a pinched spray pot, in a 4-cutting, 6" pot, given 1 application of 2500 p.p.m. B-9 approx. 2 weeks after pinching and 8 week tall treatment (1-2 weeks of long days) during the various seasons of recommended use (January thru December) as defined in the timetables published by Yoder Brothers, Inc., Barberton, Ohio. | Approximately 8"-10" when grown as a pinched spray pot, in a 4-cutting, 6" pot, given 1 application of 2500 p.p.m. B-9 approx. 2 weeks after pinching and 10 week tall treatment (1-2 weeks of long days) during the various seasons of recommended use (April thru November 15) as defined in the timetables published by Yoder Brothers, Inc., Barberton, Ohio. | Apprxomately 8"-10" when grown as a pinched spray pot, in a 4-cutting, 6" pot given 1 application of 2500 p.p.m. B-9 approx. 2 weeks after pinching and 10 week tall treatment (1-2 weeks of long days) during the various seasons of recommended use (April thru November 15) as defined in the timetables published by Yoder Brothers, Inc., Barberton, Ohio. |
| Foliage: | | | |
| Top side | Green, 7.5GY3/4. | | |
| Size | Length to width ratio 23:14 with length to 5¾" and width to 3½". | Length to width ratio 3:2 with length to 6" and width to 4". | Length to width ratio 3:2 with length to 6" and width to 4". |
| Quantity | Numerous | | |
| Shape | Spatulate lobed | | |
| Texture | Smooth | Coarse | Coarse. |
| Ribs and veins | Slight prominence | Very prominent | Very prominent. |
| Edge | Deeply indented | | |
| Serration | Coarse | Moderate | Moderate. |
| Under side | Greyed light green, 7.5GY5/4. | Greyed light green, 7.5GY5/4 | Light green, 7.5GY5/4. |
| Stipules | Prominent | | |

We claim:

1. A new and distinct cultivar of chrysanthemum characterized particularly as to uniqueness when compared to the cultivars Yellow Bonnie Jean and Improved Yellow Bonnie Jean by its year round period of value; its approximately 12–16 days earlier response when grown as a pinched spray pot; a semi-spreading habit with approximately 2" more spread as a pinched plant; excellent breaking action from a pinch, averaging one more break per plant than Yellow Bonnie Jean and Improved Yellow Bonnie Jean; 4" less vigor when given the same tall treatment; less prominent foliar veination; no known sensitivity to commonly used greenhouse chemicals; a uniform flowering response under midwinter conditions; reduced pollen production; adaptability to all pot sizes; and by its light yellow flower color, which is similar to the flower color of Yellow Bonnie Jean but distinctive relative to the darker yellow flower color of Improved Yellow Bonnie Jean.

No references cited.

ROBERT E. BAGWILL, Primary Examiner